(12) United States Patent
Carvin et al.

(10) Patent No.: US 8,987,511 B2
(45) Date of Patent: Mar. 24, 2015

(54) PROCESS FOR PRODUCING ADIPIC ACID CRYSTALS

(75) Inventors: Philippe Carvin, Lyons (FR); Stéphanie Foucher, Meyzieu (FR)

(73) Assignee: Rhodia Operations, Aubervilliers (FR)

( * ) Notice: Subject to any disclaimer, the term of this patent is extended or adjusted under 35 U.S.C. 154(b) by 790 days.

(21) Appl. No.: 13/260,267

(22) PCT Filed: Jun. 7, 2010

(86) PCT No.: PCT/EP2010/057924
§ 371 (c)(1),
(2), (4) Date: Oct. 20, 2011

(87) PCT Pub. No.: WO2010/145961
PCT Pub. Date: Dec. 23, 2010

(65) Prior Publication Data
US 2012/0095263 A1    Apr. 19, 2012

(30) Foreign Application Priority Data

Jun. 16, 2009    (FR) .................................... 09 54014

(51) Int. Cl.
*C07C 51/42*    (2006.01)
*C07C 51/43*    (2006.01)

(52) U.S. Cl.
CPC ...................... *C07C 51/43* (2013.01)
USPC .......................................................... 562/593

(58) Field of Classification Search
USPC .......................................................... 562/593
See application file for complete search history.

(56) References Cited

U.S. PATENT DOCUMENTS 5,471,001 A    11/1995    Anderson et al.
6,822,117 B1   11/2004    Felix et al.

FOREIGN PATENT DOCUMENTS

FR    2 795 721 A1    1/2001

OTHER PUBLICATIONS

International Search Report (PCT/ISA/210) issued on Sep. 7, 2010, by European Patent Office as the International Searching Authority for International Application No. PCT/EP2010/057924.
Gu et al., "Relationship between Particle Size and Impurity Incorporation during Crystallization of (+)-Pseudoephedrine Hydrochloride, Acetaminophen, and Adipic Acid from Aqueous Solution," Pharmaceutical Research, Jul. 2002, pp. 1068-1070, V. 19—No. 7.

*Primary Examiner* — Shawquia Jackson
(74) *Attorney, Agent, or Firm* — Dentons US LLP

(57) ABSTRACT

A method for producing crystals of adipic acid is described. In particular, a method for recovering adipic acid in the form of crystals with low impurity content, obtained by crystallization steps in particular using reaction media for synthesizing adipic acid is described. A purification method including a step of crushing the crystals for easier removal or the migration of the impurities in the crystals is also described.

14 Claims, No Drawings

PROCESS FOR PRODUCING ADIPIC ACID CRYSTALS

This application claims priority under 35 U.S.C. §119 of FR 0954014, filed Jun. 16, 2009, and is the United States national phase of PCT/EP2010/057924, filed Jun. 7, 2010, and designating the United States (published in the French language on Dec. 23, 2010, as WO 2010/145961 A1; the title and abstract were also published in English), each hereby expressly incorporated by reference in its entirety and each assigned to the assignee hereof.

The present invention relates to a process for producing adipic acid crystals.

It relates, more particularly, to a process for recovering adipic acid in the form of crystals having a low content of impurities, which are obtained by crystallization steps starting from, in particular, adipic acid synthesis reaction media. The expression "content of impurities" should be understood to mean the concentration of impurities other than water.

Adipic acid is a major chemical used in numerous applications either as an intermediate compound or as an additive for modifying the properties of certain products.

Among these applications, the use of adipic acid as a monomer in the production of polymers is the most important. Thus, adipic acid is one of the main monomers for the manufacture of polyamides, especially polyamide 6,6. It is also used for the manufacture of polyesters, polyester phenols, and in the production of polyurethanes.

In these applications and especially in the uses as a monomer for the production of polyamides, the adipic acid must have a very high degree of purity, that is to say a purity of a degree at least equivalent to the purity required for the active compounds used as medicaments. Moreover, the adipic acid crystals must have certain physical properties, especially size and shape properties, in order to obtain good flowability during the feeding of adipic acid into the reactors or storage tanks and also a low aptitude for caking during storage and transport. Furthermore, the presence of crystals of very small size, generally known as "fines", must be minimized for hygiene reasons during the handling of adipic acid.

Adipic acid is, in particular, synthesized by oxidation of hydrocarbons, for example of cyclohexane, either directly or in two steps.

The process that is most used industrially is the process of oxidation of cyclohexane in two steps, comprising a first step of oxidation of cyclohexane with oxygen to a cyclohexanol/cyclohexanone mixture, then oxidation of this mixture to adipic acid with nitric acid. The first oxidation of cyclohexane to cyclohexanol/cyclohexanone may be carried out in a single step or in two phases by producing, in a first stage, cyclohexyl hydroperoxide in the absence of catalyst, then, in a second phase, the decomposition of the cyclohexyl hydroperoxide to cyclohexanol/cyclohexanone, in the presence of a catalyst.

Adipic acid is also produced by nitric acid oxidation of cyclohexanol produced from benzene by hydrogenation to cyclohexene and hydration to cyclohexanol.

In these methods of synthesis, the adipic acid is present in dissolved form in the reaction medium which generally comprises water, nitric acid and numerous synthesis by-products such as diacids other than adipic acid such as glutaric and succinic acids and compounds, especially metallic compounds, originating from the catalysts used and from the corrosion of the equipment.

The adipic acid is recovered from this reaction medium generally by crystallization after cooling and/or concentrating the reaction medium. This adipic acid is purified by successive crystallizations preferably in water, then dried in order to reduce the water content and thus avoid the problems of caking or agglomeration during the storage and transport of the crystals.

In order to obtain a high degree of purity, the processes used comprise numerous steps of crystallization with significant washing and drying phases which consume energy and investment costs.

However, these processes, in order to attain the required purity quality of the adipic acid, comprise numerous steps that adversely affect the economics of the process and the physical quality of the crystals by production of "fines", for example.

There is still a demand for a better performing adipic acid purification process that makes it possible to obtain this compound with a high purity and crystals that have physical properties compatible with their storage, transport and handling.

For this purpose, the invention proposes a process for producing adipic acid crystals by crystallization that makes it possible to more easily and more economically obtain crystals of high purity and/or that have physical properties compatible with their handling, transport and storage.

The invention proposes a process for producing adipic acid crystals from a solution of adipic acid comprising at least one step of purification by crystallization and one step of separation and recovery of the crystals.

According to the invention, this process for producing adipic acid crystals comprises a phase of grinding the crystals before the step of separation and recovery of the crystals.

The process of the invention generally comprises several intermediate steps between the crystallization step and the separation and recovery step such as, for example, filtrations, repulpings, washings. Within the meaning of the present invention, it will be understood that the expression "the step of purification by crystallization and of separation and recovery of the adipic acid crystals" encompasses both the phases of crystallization and separation and recovery and also all of the intermediate phases.

According to one advantageous embodiment of the process of the invention, the step of purification by crystallization and of separation and recovery of the adipic acid crystals comprises the following steps:
  a crystallization phase in a crystallizer optionally comprising an external circulation loop of the crystallization medium, by cooling and/or by concentrating a solution of adipic acid;
  optionally a phase of separation of the crystals formed, for example by filtration;
  optionally a phase of repulping the crystals in a liquid medium saturated with adipic acid;
  a phase of separation and recovery of the crystals, optionally with washing of the crystals.

The expression "step (or phase) of separation and recovery of the crystals" should be understood to mean the step (or phase) of the process that makes it possible to recover the adipic acid crystals before they are fed to a new purification step or a drying step. In other words, if the process uses a single step of purification by crystallization and of separation and recovery of the adipic acid crystals, then the step (or phase) of separation and recovery of the crystals will be the last step before drying. If the process uses several successive steps of purification by crystallization and of separation and recovery of the adipic acid crystals, then "the step (or phase) of separation and recovery of the crystals" may denote the last step before drying (for the last purification) or the intermediate step before a new step of purification by crystallization and of separation and recovery of the adipic acid crystals (for purifications preceding the last purification).

The crystallization phase may be carried out in a crystallizer or carried out in several crystallizers mounted in series.

The expression "repulping phase" is understood, in the context of the present invention, to mean suspending or dispersing the crystals in a liquid medium, for example a solution saturated with adipic acid.

The expression "crystal grinding phase" should be understood to mean a phase during which the adipic acid crystals are broken up, to a greater or lesser extent. The grinding has the effect of releasing or of rendering displaceable, the impurities trapped in the crystals such as, for example, the liquid of crystallization or the crystallization stock solution enclosed in the crystal which would not have been able to be removed or displaced, for example, by washing or in the repulping or filtration phases (for greater clarity, the liquid of crystallization or crystallization stock solution will be referred to as water of crystallization or crystallization mother liquor without this limiting the scope of the patent to the use of water as the liquid used for carrying out the crystallization of adipic acid).

As these crystallization mother liquors or waters of crystallization contain by-products or impurities present in the crystallization medium, the grinding of the crystals makes it possible to obtain a lower concentration of these impurities at the end of the adipic acid purification process. The grinding of the crystals is generally obtained by applying a mechanical force to the crystals, either directly to the wet crystals or to the crystals suspended in a liquid such as water, advantageously saturated with adipic acid. The processes suitable for obtaining this grinding are any standard processes for grinding solid products such as, for example, agitation, pounding, crushing.

Advantageously, the step (or phase) of separation and recovery of the crystals may be carried out by any suitable processes, such as, for example, settling, filtration, centrifugation. The processes usually used are rotary filters and also centrifugation carried out in devices known as centrifugal dryers. In the step of separation and recovery, the crystals are subjected to more or less effective washing operations. The purpose of these washing operations is especially to remove the mother liquors present at the surface of the crystals.

The process for producing adipic acid crystals may be carried out in batch mode or continuously.

According to one preferred embodiment of the invention, the solution of adipic acid is an aqueous solution of adipic acid.

According to one embodiment, when a single step of purification by crystallization and of separation and recovery of the adipic acid crystals is used, the grinding phase, before the phase of separation and recovery of the crystals, is carried out on at least one of the following media:
  on the suspension of crystals contained in the crystallizer and circulating in the optional loop external to the crystallizer with recycling of this suspension containing the ground crystals into the crystallizer;
  on the crystals contained in the medium of the optional repulping phase;
  on the wet crystals after the optional repulping phase.

According to another embodiment, when at least two successive steps of purification by crystallization and of separation and recovery of the adipic acid crystals are carried out, the grinding phase, before the phase of separation and recovery of the crystals, is carried out:
  at at least any one of the steps preceding the last step of purification by crystallization and of separation and recovery of the adipic acid crystals, and/or
  during the last step of purification by crystallization and of separation and recovery of the adipic acid crystals on at least one of the following media:
    on the suspension of crystals contained in the crystallizer and circulating in the optional loop external to the crystallizer with recycling of this suspension containing the ground crystals into the crystallizer;
    on the crystals contained in the medium of the optional repulping phase;
    on the wet crystals after the optional repulping phase.

According to one preferred embodiment of the invention, the process for producing adipic acid crystals comprises at least two successive steps of purification by crystallization.

The first step of purification by crystallization is carried out starting from adipic acid present in the synthesis reaction medium. Thus, the reaction medium may optionally be concentrated by evaporation of water then cooled in order to obtain the crystallization of adipic acid. This crystallization may be carried out in crystallizers that operate continuously or in batch mode.

The crystals obtained during the first crystallization phase are separated from the mother liquors, for example by filtration. In this embodiment, the crystals are then dispersed in a liquid such as, for example, an aqueous solution saturated with adipic acid in a repulping step before being fed into a filtration/centrifugal drying step in order to lose as much water as possible, this last filtration/centrifugal drying step corresponding to the step of separation and recovery indicated above. During this last filtration/centrifugal drying step or prior to this step, the crystals are washed in order to remove or displace as much of the mother liquors or waters of crystallization present on the surface of the crystals as possible and to replace them with water that does not contain impurities.

The adipic acid obtained in this first purification step is cooled "technical-grade adipic acid". This is because these crystals still comprise a quantity of impurities trapped in the crystal and especially inclusions of mother liquors. These inclusions cannot be reduced or displaced by washing or repulping operations.

According to one embodiment of the invention, during the first step of purification by crystallization and separation and recovery of the crystals, the crystals are ground by grinding the crystals or applying a mechanical force (strong agitation) in a suspension of crystals, for example in the suspension of crystals during the repulping operation. It is also possible to carry out this grinding by placing a grinding means such as a pump in an external circulation circuit of the suspension of crystals. The grinding may be carried out in a separate step before the crystals are fed to the repulping step.

According to another embodiment of the invention, the crystallizer comprises an external circulation loop of the crystallization medium in which a grinding device is placed. In this embodiment, the recycling of the ground crystals into the crystallizer makes it possible to carry out a seeding of the crystallization medium. As is well known in the field of crystallization, seeding makes it possible to control and modify the shape of the crystals obtained.

It is also possible to provide this crystal grinding phase in a treatment step of the crystals recovered after the repulping and centrifugal drying. In this embodiment, the crystals that have been repulped, centrifugally dried once, and optionally washed are dispersed in a liquid saturated with adipic acid, advantageously water saturated with adipic acid. The grinding of the crystals is carried out on this dispersion. The adipic acid crystals thus ground are recovered in a final step of separation and recovery by any known process, for example by filtration preferably with a washing of these crystals. Thus, the crystal grinding phase is carried out on the crystals recovered after a first repulping phase then a first phase of separation by filtration, said ground crystals then being subjected to a new repulping phase before being recovered in the separation and recovery phase.

Advantageously, the grinding of the adipic acid crystals is carried out in the first step of purification by crystallization and separation and recovery of the crystals in order to obtain adipic acid crystals of determined purity. However, it is possible to provide a crystal grinding phase in the other following crystallization steps, according to embodiments similar to those described above, especially in the crystallization step that makes it possible to obtain a high-purity adipic acid.

Advantageously, the embodiment of the process of the invention comprising a grinding step in the first step(s) of purification, especially in order to produce technical-grade adipic acid, makes it possible to obtain an adipic acid with a higher degree of purity than with a process without a grinding step. Thus, the second or final step for producing adipic acid of high purity, usually known as "purified-grade adipic acid", could be a purification process with need for less high efficiency if it is desired to obtain an adipic acid with a degree of purity equivalent to that obtained with the standard processes. Equally, this purification process could make it possible to be less damaging for the shape and size of the crystals. Thus, the process of the invention makes it possible to produce adipic acid either with a very high purity or with a purity equivalent to that obtained with the standard processes but with, in particular, a lower content of fines that makes it possible to reduce the caking ability of the crystals.

In order to determine the concentration of impurities or the degree of purity of the adipic acid, the concentrations of glutaric and succinic diacids are measured and also the concentration of nitrate ions.

Other details and advantages of the invention will appear more clearly in light of the examples given below solely by way of illustration and indication.

EXAMPLE 1

Comparative

A reaction medium originating from the process of nitric acid oxidation of a cyclohexanol/cyclohexanone mixture contains around 24% by weight of adipic acid. This medium comprises water, nitric acid, various compounds derived from the oxidation reaction, nitrate ions and metal ions originating from the catalyst used and from the corrosion of the equipment.

This medium was fed into a crystallizer. The crystallization of adipic acid was obtained by cooling to a temperature of around 25° C. The crystallized solid was separated from the crystallization mother liquors by filtration.

The crystals thus recovered were suspended in water saturated with adipic acid at a temperature of 25° C. in a step known as "repulping". The crystals thus treated were fed into a filter. The crystals recovered had an average size of 437 µm.

The crystals thus filtered were washed thoroughly by supplying water saturated with adipic acid in order to thus completely displace the waters of crystallization present around the crystals. This washing method made it possible to eliminate any impurities not contained in the inclusions present in the crystals.

The crystals recovered were analysed in order to determine the concentration of glutaric acid, succinic acid and nitrate ions. The contents of glutaric and succinic acid and also those of nitrate ions were obtained by liquid phase chromatography after preparation of the sample by dilution in water and comparison with an external standard under the same conditions. The equipment used comprised a column of C18 ODS2 type, with conductometric detection or spectroscopic detection or UV detection in particular for the nitrate ions. The eluting solution was a dilute aqueous solution of a mineral or organic acid.

The results obtained were:
nitrate ions: 723 ppm
succinic acid: 159 ppm
glutaric acid: 202 ppm

EXAMPLE 2

Invention

Example 1 was repeated. The crystals present in the repulping step were subjected to a grinding operation using an ULTRA-TURRAX device placed in the repulping dispersion.

The crystals recovered after filtration and washing operations according to the process described in Example 1 had the following concentrations of impurities:
nitrate ions: 283 ppm
succinic acid: 70 ppm
glutaric acid: 82 ppm The crystals recovered had an average dimension of 120 µm.

The invention claimed is:

1. A process for producing adipic acid crystals from a solution of adipic acid, the process comprising at least one step of purification by crystallization and one step of separation and recovery of the adipic acid crystals, wherein the adipic acid crystals are subjected, before the separation and recovery step, to a grinding phase.

2. The process according to claim 1, wherein the step of purification by crystallization and of separation and recovery of the adipic acid crystals comprises the following steps:
 a crystallization phase in a crystallizer optionally comprising an external circulation loop of a crystallization medium, by cooling and/or by concentrating a solution of adipic acid;
 optionally a phase of separation of the crystals formed;
 optionally a phase of repulping the crystals in a liquid medium saturated with adipic acid;
 a phase of separation and recovery of the crystals, optionally with washing of the crystals;
 and in that
 when a single step of purification by crystallization and of separation and recovery of the adipic acid crystals is used, the grinding phase, before the phase of separation and recovery of the crystals, is carried out on at least one of the following media:
  on a suspension of crystals in the crystallizer and circulating in the optional loop external to the crystallizer with recycling of this suspension comprising the ground crystals into the crystallizer;
  on crystals in a medium of the optional repulping phase;
  on wet crystals after the optional repulping phase;
 when at least two successive steps of purification by crystallization and of separation and recovery of the adipic acid crystals are carried out, the grinding phase, before the phase of separation and recovery of the crystals, is carried out, at least any one of the steps preceding the last step of purification by crystallization and of separation and recovery of the adipic acid crystals and/or during the last step of purification by crystallization and of separation and recovery of the adipic acid crystals, on at least one of the following media:
- on the suspension of crystals contained in the crystallizer and circulating in the optional loop external to the crystallizer with recycling of this suspension containing the ground crystals into the crystallizer;
- on the crystals contained in the medium of the optional repulping phase;
- on the wet crystals after the optional repulping phase.

3. The process according to claim 1, wherein the solution of adipic acid is an aqueous solution of adipic acid.

4. The process according to claim 3, wherein the adipic acid is synthesized by nitric acid oxidation of a cyclohexanol/cyclohexanone mixture or of cyclohexanol.

5. The process according to claim 3, wherein the adipic acid is synthesized by oxidation of cyclohexane with molecular oxygen.

6. The process according to claim 1, wherein the process comprises at least two successive steps of purification by crystallization of the adipic acid.

7. The process according to claim 6, wherein the first step of purification by crystallization comprises:
- a phase of crystallization in a crystallizer by cooling and/or concentrating a solution of adipic acid;
- a phase of separation of the crystals formed;
- a phase of repulping of the crystals in a liquid medium saturated with adipic acid;
- a phase of separation and recovery of the crystals, with optional washing of the crystals; and
- the grinding phase being carried out on the crystals before the phase of separation and recovery of the crystals.

8. The process according to claim 7, wherein the grinding phase of the crystals is carried out on the crystals contained in the repulping medium.

9. The process according to claim 7, wherein the grinding phase of the crystals is carried out on the wet crystals before or after the repulping phase.

10. The process according to claim 7, wherein the grinding of the adipic acid crystals is carried out on the suspension of crystals in the crystallizer and circulating in a loop external to the crystallizer with recycling of this suspension comprising the ground crystals into the crystallizer.

11. The process according to claim 7, wherein the grinding phase of the crystals is carried out on the crystals recovered after a first repulping phase then a first phase of separation by filtration, said ground crystals then being subjected to a new repulping phase before being recovered in the separation and recovery phase.

12. The process according to claim 1, wherein the separation and recovery of the crystals is carried out by filtration or centrifugal drying.

13. The process according to claim 1, wherein the separated crystals are subjected to one or more washing operations.

14. The process according to claim 1, wherein the grinding of the crystals is carried out by mechanical agitation, pounding and crushing.

* * * * *